(12) United States Patent
Liu et al.

(10) Patent No.: US 11,039,640 B2
(45) Date of Patent: Jun. 22, 2021

(54) ULTRASONIC ATOMIZATION PIECE, ELECTRONIC CIGARETTE ATOMIZATION CORE AND ELECTRONIC CIGARETTE ATOMIZER

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Wei Huang, Hunan (CN); Yuangang Dai, Hunan (CN); Xinqiang Yin, Hunan (CN); Hong Yu, Hunan (CN); Jianhua Yi, Hunan (CN); Lizhou Shen, Hunan (CN); Youlin He, Hunan (CN); Yang Wang, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 335 days.

(21) Appl. No.: 16/300,130

(22) PCT Filed: Dec. 17, 2016

(86) PCT No.: PCT/CN2016/110583
§ 371 (c)(1),
(2) Date: Nov. 9, 2018

(87) PCT Pub. No.: WO2017/202014
PCT Pub. Date: Nov. 30, 2017

(65) Prior Publication Data
US 2019/0142063 A1 May 16, 2019

(30) Foreign Application Priority Data
May 23, 2016 (CN) .......................... 201620471233.4

(51) Int. Cl.
*A24F 40/05* (2020.01)
*A24F 40/44* (2020.01)
(Continued)

(52) U.S. Cl.
CPC .............. *A24F 40/05* (2020.01); *A24F 40/44* (2020.01); *A24F 40/485* (2020.01); *A24F 47/00* (2013.01);
(Continued)

(58) Field of Classification Search
CPC ...... A24F 47/00; A24F 47/008; A24F 47/002; B05B 17/06; B05B 17/0607
See application file for complete search history.

(56) References Cited

U.S. PATENT DOCUMENTS

| 6,196,218 B1 * | 3/2001 | Voges | A24F 47/002 128/200.14 |
| 2017/0119040 A1 * | 5/2017 | Cameron | A24F 47/008 |
| 2017/0280771 A1 * | 10/2017 | Courbat | A24F 47/008 |

FOREIGN PATENT DOCUMENTS

| CN | 1085829 A | * | 4/1994 |
| CN | 1085829 A | | 4/1994 |

(Continued)

*Primary Examiner* — Alex B Efta
(74) *Attorney, Agent, or Firm* — Mauriel Kapouytian Woods LLP; Liang Huang; Michael Mauriel (57) ABSTRACT

Disclosed are an ultrasonic atomization piece, an electronic cigarette atomization core and an electronic cigarette atomizer. The ultrasonic atomization piece includes a piezoelectric ceramic main body; one surface of the piezoelectric ceramic main body is in contact with a positive electrode conducting layer, and the other surface of the piezoelectric ceramic main body is in contact with a negative electrode conducting layer, the negative electrode conducting layer extends to the surface of the piezoelectric ceramic main body on which the positive electrode conducting layer is located along a side edge of the piezoelectric ceramic main (Continued)

body, and a plurality of convex point areas, which cover the edge of the positive electrode conducting layer are provided on an edge of the negative conductive layer. The ultrasonic atomization piece, the electronic cigarette atomization core and the electronic cigarette atomizer have the advantages of simple structure, reliable electrical connection, reliable work, high atomization speed, good smoke taste and long service life.

16 Claims, 9 Drawing Sheets

(51) Int. Cl.
    *A24F 40/485*     (2020.01)
    *A24F 40/10*     (2020.01)
    *A24F 47/00*     (2020.01)
    *B05B 17/06*     (2006.01)

(52) U.S. Cl.
    CPC .......... *B05B 17/06* (2013.01); *B05B 17/0607* (2013.01); *A24F 40/10* (2020.01)

(56) References Cited

FOREIGN PATENT DOCUMENTS

| | | | |
|---|---|---|---|
| CN | 2912831 Y | | 6/2007 |
| CN | 203448228 U | * | 2/2014 |
| CN | 203448228 U | | 2/2014 |
| CN | 104368484 A | | 2/2015 |
| CN | 105559151 A | | 5/2016 |
| JP | 2008207055 A | | 9/2008 |
| JP | 2010142737 A | | 7/2010 |

* cited by examiner

ULTRASONIC ATOMIZATION PIECE, ELECTRONIC CIGARETTE ATOMIZATION CORE AND ELECTRONIC CIGARETTE ATOMIZER

CROSS REFERENCE TO RELATED APPLICATIONS

This application is a national phase application of international application number PCT/CN2016/110583 filed on Dec. 17, 2016, which claims priority to Chinese application number 201620471233.4 filed on May 23, 2016. The entire contents of these applications are hereby incorporated herein by reference.

TECHNICAL FIELD

The present invention belongs to the technical field of electronic cigarette, and particularly relates to an ultrasonic atomization piece, an electronic cigarette atomization core and an electronic cigarette atomizer.

BACKGROUND ART

The existing ultrasonic electronic cigarette has the following shortcomings at work:

Firstly, an ultrasonic atomization piece includes a piezoelectric ceramic main body, one surface of the piezoelectric ceramic main body is in contact with a positive electrode conducting layer, the other surface of the piezoelectric ceramic main body is in contact with a negative electrode conducting layer, and the positive electrode conducting layer and the negative electrode conducting layer are electrically connected by a welded conducting wire. Since the ultrasonic atomization piece will produce oscillation at work, the positive electrode conducting layer and the negative electrode conducting layer will be continuously impacted, such that the conducting wire is disconnected at the welding place and is damaged easily, which affects the reliability of circuit connection, and leads to unreliable work and a short service life.

Secondly, as the ultrasonic atomization piece will produce air pressure at work, a liquid guide body covered on the surface of the ultrasonic atomization piece will be impacted, resulting in the fact that the ultrasonic atomization piece is not laminated with the liquid guide body, which leads to idle vibration of the ultrasonic atomization piece, affects the atomization effect and causes a shortened service life of the ultrasonic atomization piece easily.

CONTENTS OF INVENTION

The existing ultrasonic atomization piece has the shortcomings of unreliable circuit connection, unreliable work, poor atomization effect and short service life. The objective of the present invention is to provide an improved ultrasonic atomization piece, an improved electronic cigarette atomization core and an improved electronic cigarette atomizer in view of the shortcomings of the above prior art. The present invention has the beneficial effects that the circuit connection is reliable, the work is reliable, the atomization effect is good, and the service life is long.

In order to solve the above-mentioned technical problems, the technical solution adopted by the present invention is as follows:

An ultrasonic atomization piece includes a piezoelectric ceramic main body; one surface of the piezoelectric ceramic main body is in contact with a positive electrode conducting layer; and the other surface of the piezoelectric ceramic main body is in contact with a negative electrode conducting layer, the ultrasonic atomization piece is structurally characterized in that the negative electrode conducting layer extends to the surface of the piezoelectric ceramic main body on which the positive electrode conducting layer is located along a side edge of the piezoelectric ceramic main body, and a plurality of convex point areas which cover the edge of the positive electrode conducting layer are provided on the edge of the negative electrode conducting layer.

By means of the above structure, the negative electrode conducting layer, the piezoelectric ceramic main body and the positive electrode conducting layer form an entirety, thereby simplifying the conducting structure, meanwhile, the negative electrode conducting layer is unlikely to be broken off by the oscillation of the piezoelectric ceramic main body, therefore the electrical connection is reliable, the working reliability is high, and the service life is long.

Based on the same inventive concept, the present invention further provides an electronic cigarette atomization core, including the above-mentioned ultrasonic atomization piece.

As a preferred mode, the electronic cigarette atomization core includes a first sleeve, a second sleeve, a first liquid guide body and a second liquid guide body; one end of the first sleeve is provided in the second sleeve; the first liquid guide body is fixed between the first sleeve and the second sleeve, and one end of the first liquid guide body is in contact with the second liquid guide body; a liquid inlet hole is provided in the second sleeve, and the first liquid guide body is communicated with the liquid inlet hole; and the second liquid guide body is in contact with the ultrasonic atomization piece.

Further, the second sleeve is provided in a liquid control ring; and an adjusting hole is provided in the liquid control ring.

The size of the liquid inlet hole can be adjusted by rotating the liquid control ring so as to control the liquid amount.

The ultrasonic atomization piece is provided in a mounting base.

As a preferred mode, the mounting base is provided in a bottom part of the second sleeve, the first liquid guide body is fixed in the mounting base, and the second liquid guide body and the first liquid guide body are sequentially arranged along an outflow direction of the atomizing gas. This structure guides tobacco tar from top to bottom, the flow speed of the tobacco tar is relatively high under the action of gravity, and thus the tobacco tar is applied to an atomization core which requires a higher liquid guide speed.

As another preferred mode, the mounting base is provided in a top part of the first sleeve, the second liquid guide body is provided on the mounting base, and the side edge of the second liquid guide body stretches out from the mounting base and is in contact with the first liquid guide body; the top end of the second sleeve is detachably connected with a top cover; and the first liquid guide body and the second liquid guide body are sequentially arranged along the outflow direction of the atomizing gas. This structure leads to a relatively slow liquid guide speed, and thus a tobacco tar submersion phenomenon on the surface of the ultrasonic atomization piece can be better prevented.

Further, at least one through hole is provided in the second liquid guide body.

As a preferred mode, at least one minipore which penetrates through the ultrasonic atomization piece is provided in the ultrasonic atomization piece.

Further, a vent groove is provided in the surface in which the ultrasonic atomization piece is in contact with the second liquid guide body.

Further, a depression part is provided at the middle of the second liquid guide body, and the through hole is provided in the depression part.

The minipore can enable the gas to pass by, but the liquid cannot pass by, therefore it is convenient to take away the smoke on the surface of the second liquid guide body, and the atomization efficiency is improved. Due to the vent groove, the airflow passes between the ultrasonic atomization piece and the second liquid guide body and is mixed with the atomized smoke, so that the smoke is finer and smoother, and the particle sizes of granules are more uniform. Meanwhile, due to the deployment of the through hole or the vent groove, the contact area between the ultrasonic atomization piece and the second liquid guide body can be reduced, therefore, the consumption energy absorbed by the second liquid guide body is reduced, the start up speed of the ultrasonic atomization piece is high, and the user experience is improved; and moreover, it can also be avoided that the air pressure produced by the work of the ultrasonic atomization piece flushes the second liquid guide body away from the ultrasonic atomization piece, therefore, the lamination between the second liquid guide body and the ultrasonic atomization piece is better, and the normal supply of tobacco tar is not affected.

Based on the same inventive concept, the present invention further includes an electronic cigarette atomizer, including the electronic cigarette atomization core in any one of the above solutions, a liquid storage cavity and an airflow passage; wherein the liquid storage cavity is communicated with the liquid inlet hole; and one surface, away from the ultrasonic atomization piece, of the second liquid guide body is communicated with the airflow passage.

When the electronic cigarette atomization core in the first solution is adopted, the airflow passage includes an air outlet pipe provided in the first sleeve; an air inlet passage is provided between an inner wall of the first sleeve and an outer wall of the air outlet pipe; the bottom end of the air outlet pipe is communicated with an upper surface of the second liquid guide body; the top end of the air outlet pipe is in fixed connection with a suction nozzle base, and the air outlet pipe is communicated with the inner cavity of a suction nozzle on the suction nozzle base; an air inlet is provided in the suction nozzle base; and the air inlet passage is communicated with the air inlet and the surface, away from the ultrasonic atomization piece, of the second liquid guide body. The bottom end of the second sleeve is provided in the top part of an outer ring; a second fixing ring is provided in the outer ring; an insulating ring is provided in the second fixing ring; a negative electrode spring is provided at the outside of the insulating ring; a positive electrode spring is provided in the insulating ring; and the negative electrode spring is in contact with the negative electrode conducting layer of the ultrasonic atomization piece through a negative electrode ring, and the positive electrode spring is in contact with the positive electrode conducting layer of the ultrasonic atomization piece through a positive electrode ring. The structure is compact.

When the electronic cigarette atomization core in the second solution is adopted, the airflow passage includes an air outlet pipe whose bottom end is provided in the top cover; an air inlet passage is provided between the air outlet pipe and the top cover; the bottom end of the air outlet pipe is communicated with the upper surface of the second liquid guide body; the top end of the air outlet pipe is in fixed connection with a suction nozzle base, and the air outlet pipe is communicated with the inner cavity of a suction nozzle on the suction nozzle base; an air inlet is provided in the suction nozzle base; and the air inlet passage is communicated with the air inlet and the second liquid guide body. A base is provided in the first sleeve; a bottom plug is provided on the base, and the top end of the bottom plug stretches into the insulating ring; a negative electrode spring is provided at the outside of the insulating ring; a positive electrode spring is provided in the insulating ring; and the negative electrode spring is in contact with the negative electrode conducting layer of the ultrasonic atomization piece through a negative electrode ring, and the positive electrode spring is in contact with the positive electrode conducting layer of the ultrasonic atomization piece through a positive electrode ring. The structure is compact.

Compared with the prior art, the present invention has the advantages of simple structure, reliable electrical connection, reliable work, high atomization speed, good smoke taste and long service life.

SPECIFIC MODE FOR CARRYING OUT THE INVENTION

A specific implementation process of the present invention will be illustrated below in combination with the drawings. The so-called top end below all refers to the end close to a suction nozzle of an atomizer, namely the end on an outflow direction of the atomizing gas; and so-called bottom end refers to the end opposite to the position of the top end.

Figure 1:
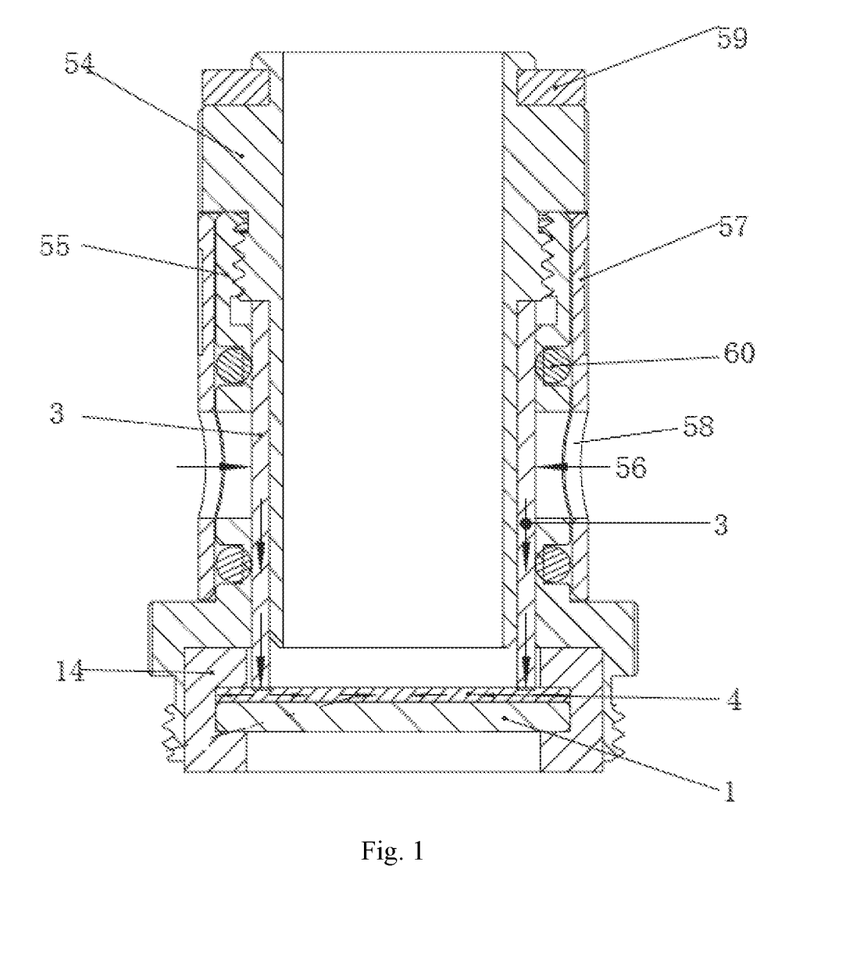
FIG. 1 is a sectional view of an atomization core in embodiment 1 of the present invention.

As shown in FIG. 1, atomization core in embodiment 1 of the present invention includes a first sleeve 54 and a second sleeve 55; an ultrasonic atomization piece 1 is provided on one end of the second sleeve 55, the other end of the second sleeve 55 is in fixed connection with the first sleeve 54, a connecting end of the first sleeve 54 extends to the surface of the ultrasonic atomization piece 1 and is not in contact with the ultrasonic atomization piece 1; the part below a top end of the first sleeve 54 is provided in the second sleeve 55; a first liquid guide body 3 is fixed between the first sleeve 54 and the second sleeve 55, one end of the first liquid guide body 3 extends along the axial direction of the first sleeve 54 to contact with the surface of a second liquid guide body 4; a liquid inlet hole 56 is provided in the second sleeve 55; and the second liquid guide body 4 is in contact with the ultrasonic atomization piece 1.

The second sleeve 55 is provided in a liquid control ring 57; and an adjusting hole 58 is provided in the liquid control ring 57.

Figure 2:
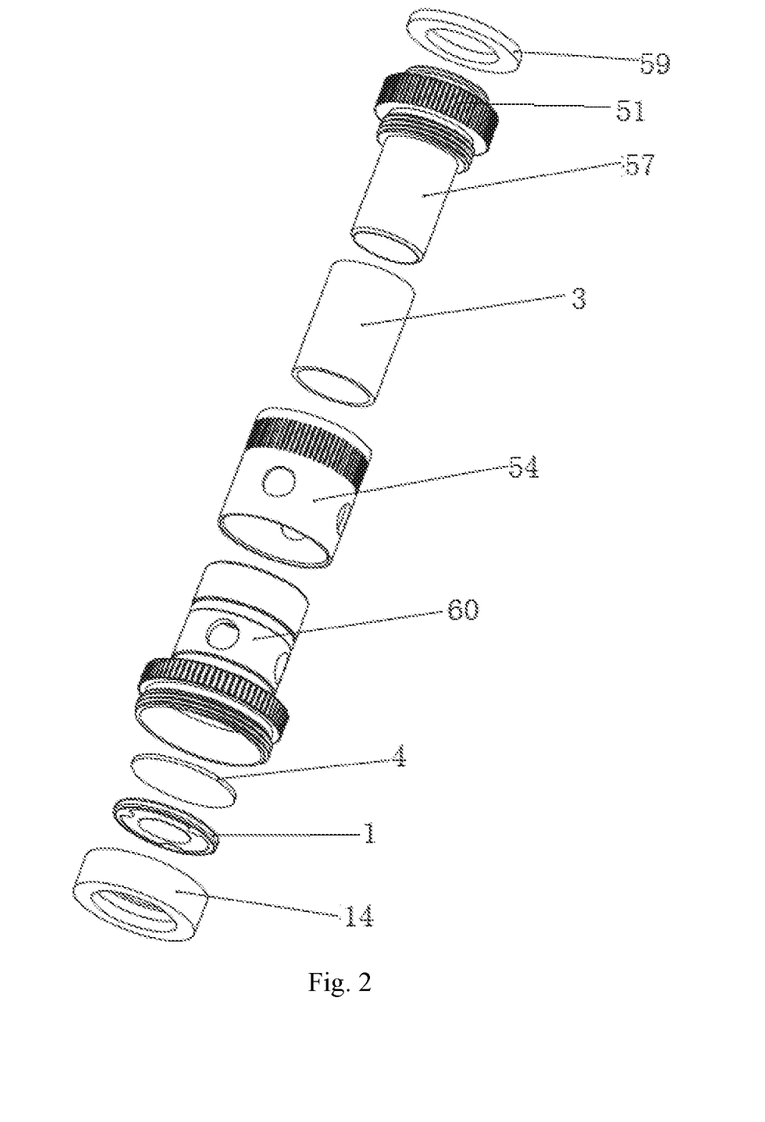
FIG. 2 is an explosive view of an atomization core in embodiment 1 of the present invention.

As shown in FIG. 2, the first liquid guide body 3 is cylindrical tobacco tar guide cotton with two open ends and is sheathed on the first sleeve. The thickness of the side wall of a top end of the first sleeve is larger than the thickness of the side wall of the rest part (actually, a boss 51 is formed on an outer wall of the top end of the first sleeve), after thread below the boss at the top end of the second sleeve is in screw joint with the first sleeve, a liquid control ring (being a cylinder with two open ends actually) is sheathed at the outside of the second sleeve, the liquid control ring can be rotated, when the adjusting hole is overlapped with the liquid inlet hole, the liquid inlet volume is the largest, when the adjusting hole is stagger to the liquid inlet hole, the liquid inlet volume is reduced, and the liquid inlet hole is even closed.

A silica gel piece 59 is provided on the first sleeve on one end, away from the liquid control ring, of the boss 51.

In order to prevent tobacco tar leakage of the atomization core, the liquid control ring is hermetically connected with the second sleeve through a sealing ring 60.

The ultrasonic atomization piece 1 is provided in a mounting base 14, the mounting base 14 is provided in a bottom part of the second sleeve 55, the first liquid guide body 3 is fixed in the mounting base 14, and the second liquid guide body 4 and the first liquid guide body 3 are sequentially arranged along an outflow direction of the atomizing gas.

The mounting base can be a silica gel base to buffer the oscillating force of the ultrasonic atomization piece, so as to prevent the damage of the ultrasonic atomization piece and prolong the service life of the ultrasonic atomization piece.

Figure 3:
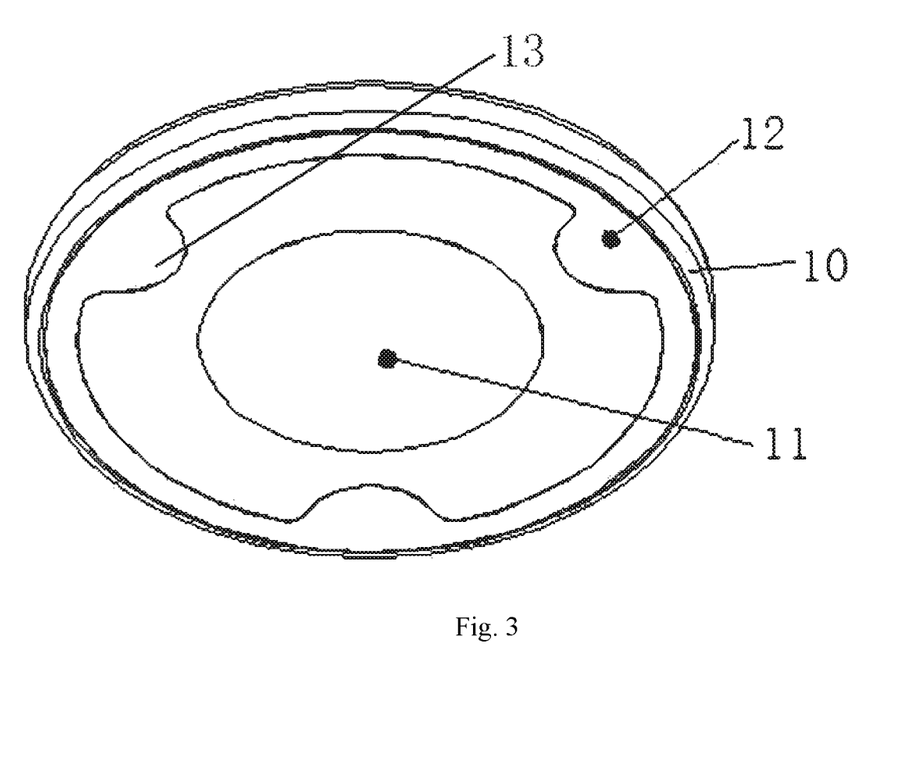
FIG. 3 is a structural schematic diagram of an ultrasonic atomization piece corresponding to embodiment 1.

As shown in FIG. 3, the ultrasonic atomization piece 1 of the present invention includes a piezoelectric ceramic main body 10; one surface of the piezoelectric ceramic main body 10 is in contact with a positive electrode conducting layer 11; and the other surface of the piezoelectric ceramic main body 10 is in contact with a negative electrode conducting layer 12, the negative electrode conducting layer 12 extends to the surface of the piezoelectric ceramic main body 10 on which the positive electrode conducting layer 11 is located along a side edge of the piezoelectric ceramic main body 10, and a plurality of convex point areas 13 (the edges of the convex points are circular arc-shaped) are provided on the edge of the negative electrode conducting layer 12. The conducting layer can be set as a silver layer.

Figure 4:
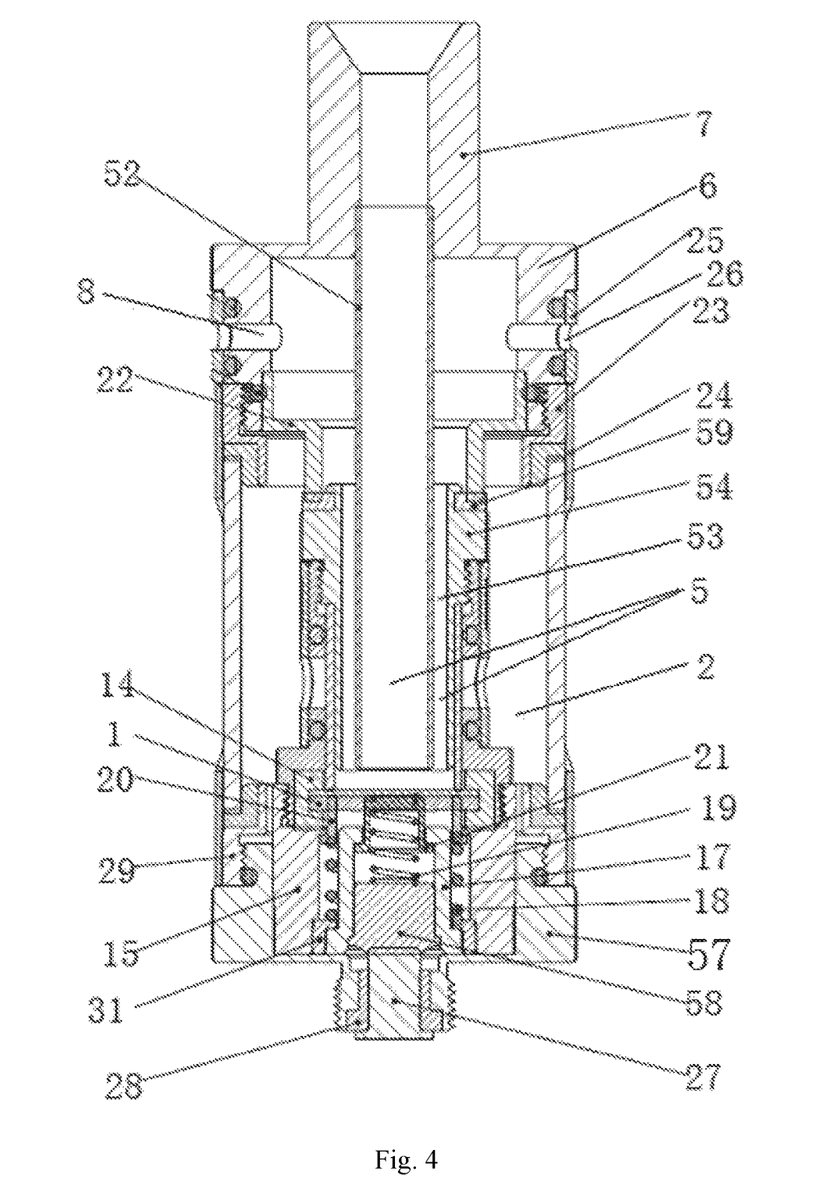
FIG. 4 is a structure diagram of an atomizer of the atomization core corresponding to embodiment 1.

The structure of the atomization core of embodiment 2 of the present invention is as shown in FIG. 4, in the embodiment, the part above the bottom end of the first sleeve 54 is provided in the second sleeve 55, the mounting base 14 is provided in the bottom part of the second sleeve 55, the first liquid guide body 3 is fixed in the mounting base 14, and the second liquid guide body 4 and the first liquid guide body 3 are sequentially arranged along the outflow direction of the atomizing gas (i.e., the liquid is transferred reverse to the gravity direction).

In embodiment 2, the mounting base 14 is provided in the top part of the first sleeve 54; the second liquid guide body 4 is provided on the mounting base 14, and the side edge of the second liquid guide body 4 stretches out from the mounting base 14 and is in contact with the first liquid guide body 3; the top end of the second sleeve 55 is connected with a top cover 9; and the first liquid guide body 3 and the second liquid guide body 4 are sequentially arranged along the outflow direction of the atomizing gas.

Figure 5:
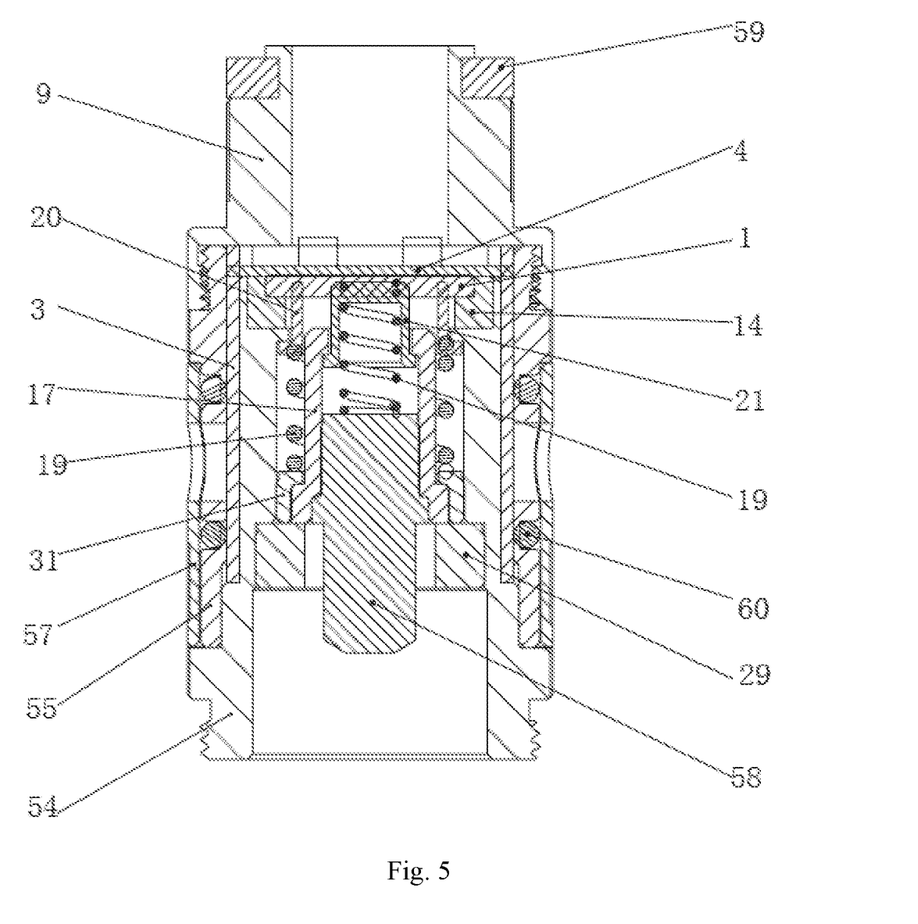
FIG. 5 is a sectional view of an atomization core in embodiment 2 of the present invention.

As shown in FIG. 5, in embodiment 2, the boss 51 is provided at the top end of the first sleeve, threads are provided on the first sleeves on both sides of the boss, the second sleeve is in screw joint with the first sleeve; and the top cover 9 is in screw joint with the top end (i.e., the upper side of the boss) of the first sleeve. The interior of the top cover 9 is of a hollow structure. The silica gel piece 59 is provided at the top end of the top cover 9.

Figure 6:
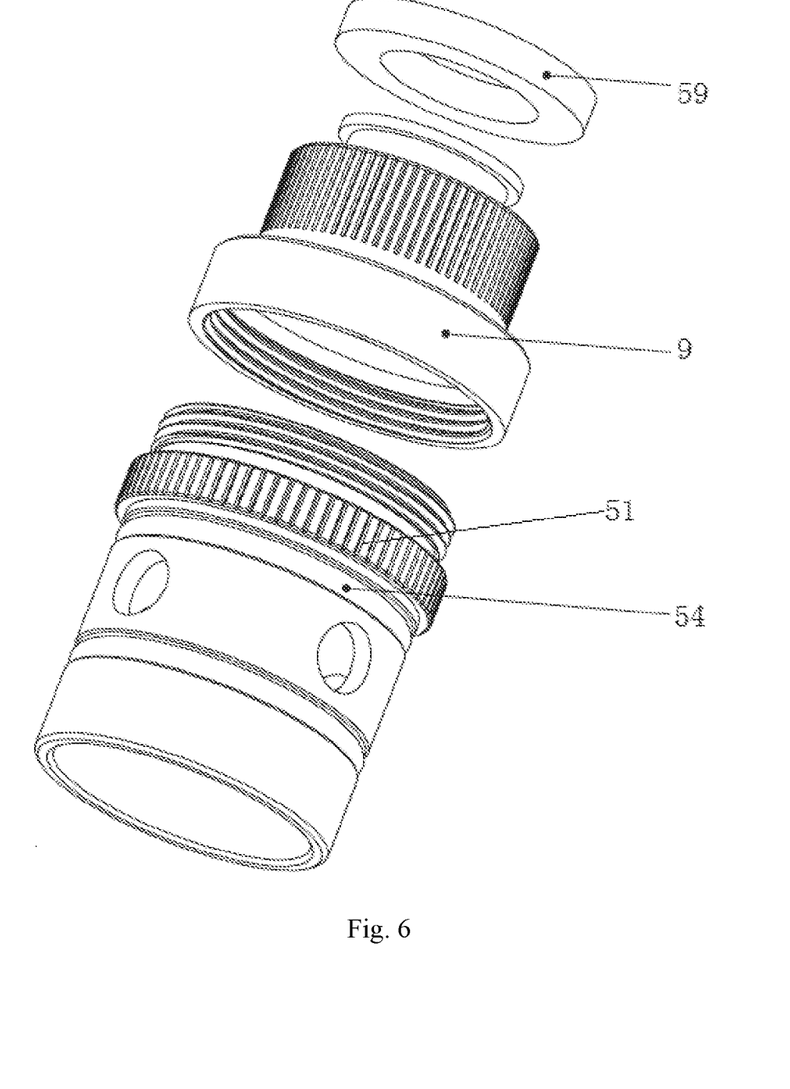
FIG. 6 is a partial explosive view of an end cover and a first sleeve of the atomization core in embodiment 2 of the present invention.

As shown in FIG. 6, in the atomizer corresponding to embodiment 1 of the present invention, a liquid storage cavity 2 is provided above the ultrasonic atomization piece 1, and the upper part of the atomization core is provided in the liquid storage cavity 1; an airflow passage 5 of the atomizer includes an air outlet pipe 52 provided in the first sleeve 54; an air inlet passage 53 is provided between the inner wall of the first sleeve 54 and the outer wall of the air outlet pipe 52; the bottom end of the air outlet pipe 52 is communicated with an upper surface of the second liquid guide body 4; the top end of the air outlet pipe 52 is in fixed connection with a suction nozzle base 6, and the air outlet pipe 52 is communicated with the inner cavity of a suction nozzle 7 on the suction nozzle base 6; an air inlet 8 is provided in the suction nozzle base 6; and the air inlet passage 53 is communicated with the air inlet 8 and the second liquid guide body 4.

As shown in FIG. 6, the silica gel piece 59 at the top end of the first sleeve is in contact with an air inlet ring 22; the outer wall of the air inlet ring 22 is in screw joint with the inner wall of an end cover 23; the end cover 23 is provided in an outer pipe 24; and the top end of the outer pipe 24 is connected with the bottom end of the suction nozzle base. Sealing rings are provided between the air inlet ring 22 and the end cover 23 and between the suction nozzle base and the outer pipe for sealing.

An air adjusting ring 25 for adjusting the air flow amount on the air inlet 8 is further provided on the suction nozzle base, an air adjusting hole 26 is provided in the air adjusting ring 25, the air adjusting ring can be rotated, and when the position of the air adjusting hole is overlapped with the position of the air inlet, the air inflow amount is the largest.

The bottom end of the second sleeve 55 is provided in the top part of the outer ring 15; a fixing ring 16 is provided in the outer ring 15; an insulating ring 17 is provided in the fixing ring 16; a negative electrode spring 18 is provided at the outside of the insulating ring 17; a positive electrode spring 19 is provided in the insulating ring 17; and the negative electrode spring 18 is in contact with the negative electrode of the ultrasonic atomization piece 1 through a negative electrode ring 20, and the positive electrode spring 19 is in contact with the positive electrode of the ultrasonic atomization piece 1 through a positive electrode ring 21.

The outer ring 15 is provided in a base 57, and the top end of the base is in screw joint with the bottom end of the outer pipe 24 and seals the liquid storage cavity. A bottom plug 58 is provided on the base 57, and the top end of the bottom plug 58 stretches into the insulating ring 17; a negative electrode spring 18 is provided at the outside of the insulating ring 17; a positive electrode spring 19 is provided in the insulating ring 17; the positive electrode spring 19 is in contact with the top end of the bottom plug; and the negative electrode spring 18 is in contact with the negative electrode of the ultrasonic atomization piece 1 through a negative electrode ring 20, and the positive electrode spring 19 is in contact with the positive electrode of the ultrasonic atomization piece 1 through a positive electrode ring 21. The bottom end of the bottom plug 58 is in contact with an electrode ring 27, and the electrode ring 27 is provided in the inner part of the lower end of the base and is insulated from the base by an insulating part 28.

Figure 7:
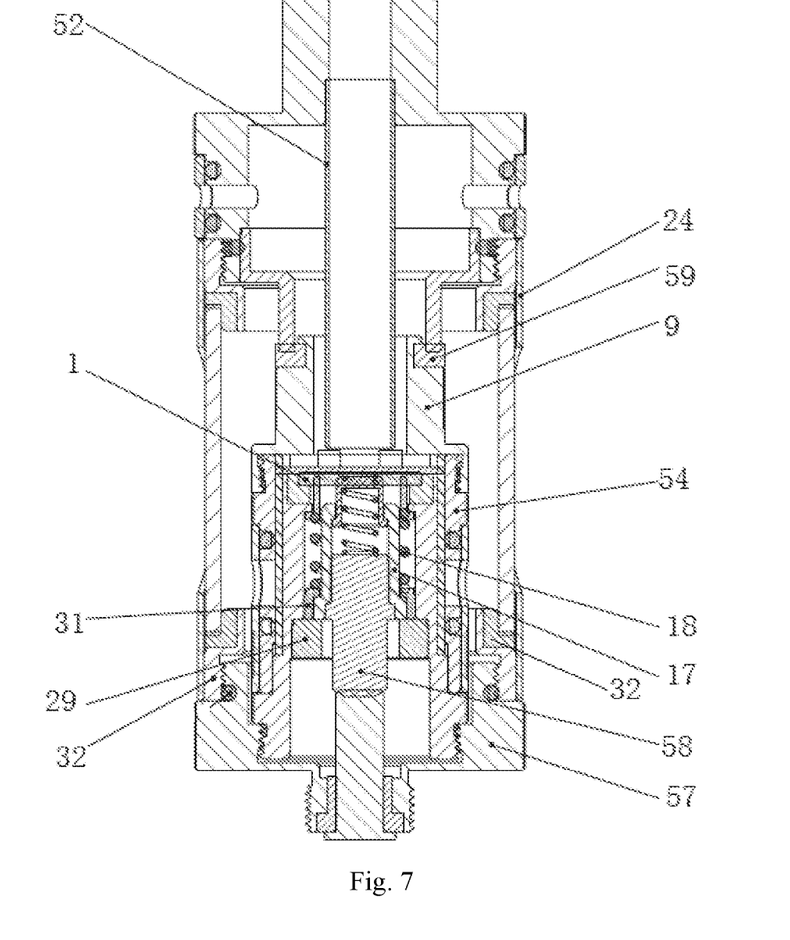
FIG. 7 is a structural schematic diagram of an atomizer in embodiment 2 of the present invention.

As shown in FIG. 7, when the atomization core in embodiment 2 is adopted, the airflow passage 5 includes the air outlet pipe 52 whose bottom end is provided in the top cover 9; the air inlet passage 53 is provided between the air outlet pipe 52 and the top cover 9; the bottom end of the air outlet pipe 52 is communicated with the upper surface of the second liquid guide body 4; the top end of the air outlet pipe 52 is in fixed connection with the suction nozzle base 6, and the air outlet pipe 52 is communicated with the inner cavity of the suction nozzle 7 on the suction nozzle base 6; the air inlet 8 is provided in the suction nozzle base 6; and the air inlet passage 53 is communicated with the air inlet 8 and the second liquid guide body 4.

The top cover 9 is in contact with the air inlet ring 22; the outer wall of the air inlet ring 22 is in screw joint with the inner wall of the end cover 23; the end cover 23 is provided in the outer pipe 24; and the top end of the outer pipe 24 is connected with the bottom end of the suction nozzle base 6. Sealing rings are provided between the air inlet ring 22 and the end cover 23 and between the suction nozzle base 6 and the outer pipe for sealing.

A bottom ring 29 is provided in the first sleeve 54; the bottom plug 58 is provided on the bottom ring 29, and the top end of the bottom plug 58 stretches into the insulating ring 17; the negative electrode spring 18 is provided at the outside of the insulating ring 17; the positive electrode spring 19 is provided in the insulating ring 17; and the negative electrode spring 18 is in contact with the negative electrode of the ultrasonic atomization piece 1 through a negative electrode ring 20, and the positive electrode spring 19 is in contact with the positive electrode of the ultrasonic atomization piece 1 through a positive electrode ring 21.

The bottom end of the bottom plug 58 is in contact with the electrode ring 27, the electrode ring 27 is provided in the inner part of the lower end of the base and is insulated from the base by the insulating part 28, the top end of the base 57 is in fixed connection with a lower end cover 32, and the lower end cover 32 is connected with the bottom end of the outer pipe through a first fixing ring 30 and seals the liquid storage cavity.

One end of the negative electrode spring 18 is in contact with the negative electrode ring 20, and the other end of the negative electrode spring is in contact with a second fixing ring 31 provided between the insulating ring 17 and the first sleeve 54.

Figure 8:
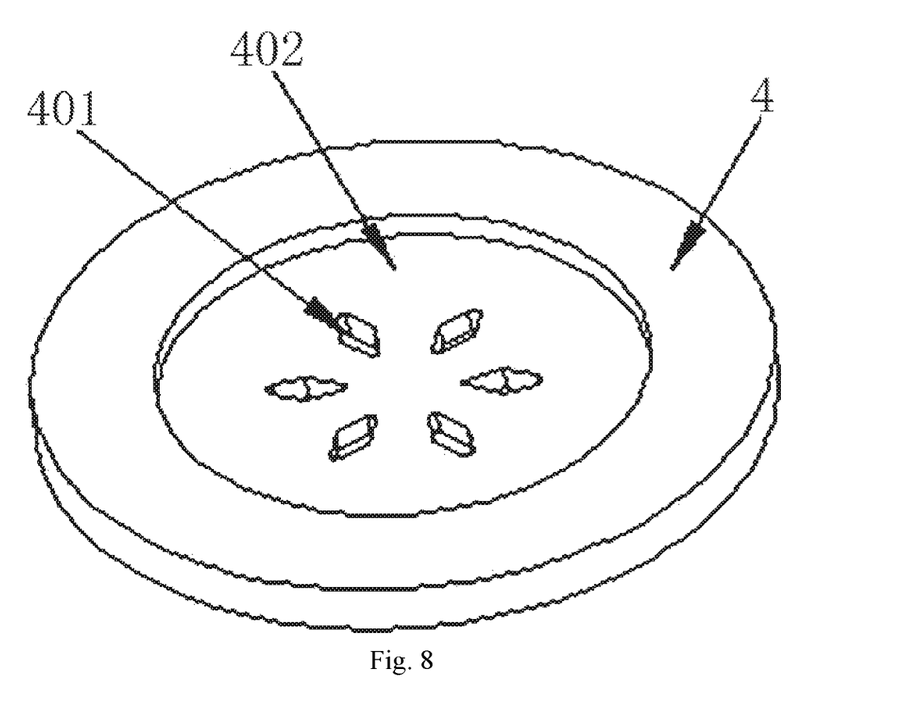
FIG. 8 is a second structural schematic diagram of a second liquid guide body of the present invention.

As shown in FIG. 8, at least one through hole 401 is provided in the second liquid guide body 4. A depression part 402 is provided at the middle of the second liquid guide body 4, and the through hole 401 is provided in the depression part 402. As the liquid guide cotton at the depression part 402 at the middle is thinner, the amount of the liquid absorbed by the depression part 402 is smaller, and thus the problems that the atomization is overdue caused by excessive accumulated liquid, and that the start of the ultrasonic atomization piece 1 is slow resulting from the fact that the second liquid guide body 4 absorbs the heat on the ultrasonic atomization piece 1 are solved.

Figure 9:
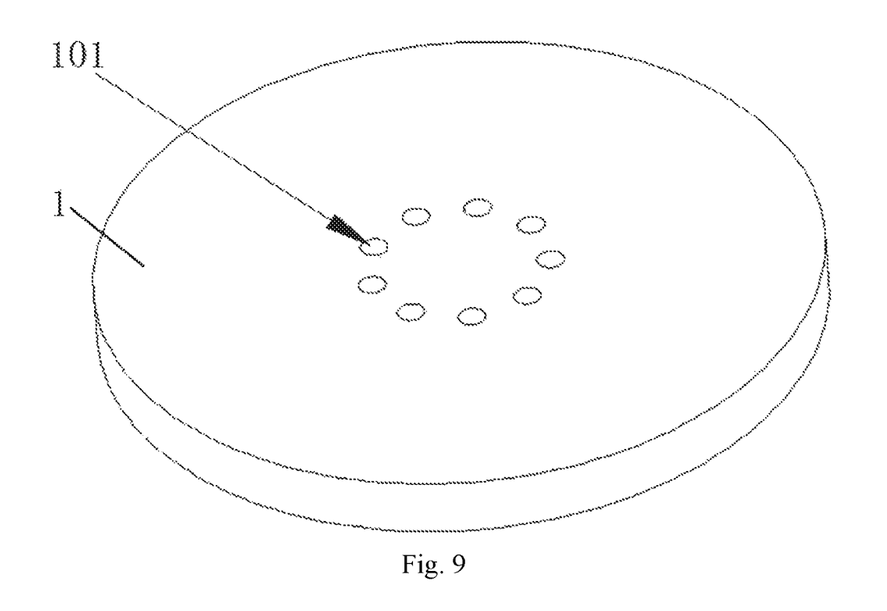
FIG. 9 is a second structural schematic diagram of the ultrasonic atomization piece of the present invention.

As shown in FIG. 9, at least one minipore 101 (the minipore 101 penetrates through the ultrasonic atomization piece 1) which is communicated with the through hole 401 is provided in the ultrasonic atomization piece 1, the aperture of the minipore 101 is about 0.1-200 microns, thereby guaranteeing that the liquid cannot pass by the minipore 101 and only the gas can pass by.

Figure 10:
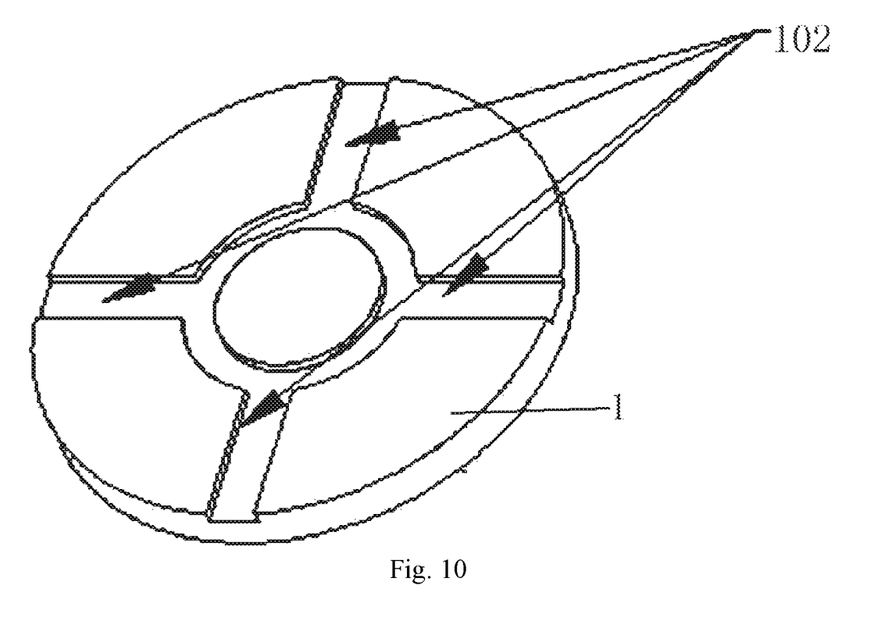
FIG. 10 is a third structural schematic diagram of the ultrasonic atomization piece of the present invention.

As shown in FIG. 10, a vent groove 102 (the surface provided with the vent groove 102 of the ultrasonic atomization piece 1 is in contact with the second liquid guide body 4) is provided in the surface, opposite to the positive electrode conducting layer 11, of the ultrasonic atomization piece 1, and the vent groove 102 is communicated with the through hole 401. The airflow enters from the vent groove 102 and quickly takes away the atomizing gas on the surface of the second liquid guide body 4, so that the ultrasonic atomization piece 1 is started quickly, the atomizing gas is finer and smoother, and the particle sizes of the granules are more uniform.

Although the embodiments of the present invention have been described above in combination with the drawings, the present invention is not limited to the specific embodiments described above, and the specific embodiments described above are merely illustrative and are not restrictive, those of ordinary skilled in the art can also make a lot of forms under the enlightenment of the present invention without departing from the purpose of the present invention or the protection scope of the claims, and all these forms fall within the protection scope of the present invention.

The invention claimed is:

1. An ultrasonic atomization piece, comprising a piezoelectric ceramic main body; wherein:
    one surface of the piezoelectric ceramic main body is in contact with a positive electrode conducting layer;
    another surface of the piezoelectric ceramic main body is in contact with a negative electrode conducting layer,
    the negative electrode conducting layer extends to the surface of the piezoelectric ceramic main body on which the positive electrode conducting layer is located along a side edge of the piezoelectric ceramic main body, and
    a plurality of convex point areas which cover an edge of the positive electrode conducting layer are provided on an edge of the negative electrode conducting layer.

2. An electronic cigarette atomization core, comprising:
    an ultrasonic atomization piece comprising a piezoelectric ceramic main body; wherein:
    one surface of the piezoelectric ceramic main body is in contact with a positive electrode conducting layer;
    another surface of the piezoelectric ceramic main body is in contact with a negative electrode conducting layer,
    the negative electrode conducting layer extends to the surface of the piezoelectric ceramic main body on which the positive electrode conducting layer is located along a side edge of the piezoelectric ceramic main body, and
    a plurality of convex point areas which cover an edge of the positive electrode conducting layer are provided on an edge of the negative electrode conducting layer.

3. The electronic cigarette atomization core of claim 2, comprising: a first sleeve, a second sleeve, a first liquid guide body, and a second liquid guide body; wherein:
    one end of the first sleeve is provided in the second sleeve;
    the first liquid guide body is fixed between the first sleeve and the second sleeve, and one end of the first liquid guide body is in contact with the second liquid guide body;

a liquid inlet hole is provided in the second sleeve, and the first liquid guide body is communicated with the liquid inlet hole; and the second liquid guide body is in contact with the ultrasonic atomization piece.

4. The electronic cigarette atomization core of claim 3, wherein:
the second sleeve is provided in a liquid control ring; and
an adjusting hole is provided in the liquid control ring.

5. The electronic cigarette atomization core of claim 4, wherein:
the electronic cigarette atomization core further comprises a mounting base,
the mounting base is provided in a bottom part of the second sleeve,
the first liquid guide body is fixed in the mounting base, and
the second liquid guide body and the first liquid guide body are sequentially arranged along an outflow direction of the atomizing gas.

6. The electronic cigarette atomization core of claim 4, wherein:
the electronic cigarette atomization core further comprises a mounting base, the mounting base is provided in a top part of the first sleeve;
the second liquid guide body is provided on the mounting base, and a side edge of the second liquid guide body stretches out from the mounting base and is in contact with the first liquid guide body;
a top end of the second sleeve is detachably connected with a top cover; and
the first liquid guide body and the second liquid guide body are sequentially arranged along the outflow direction of the atomizing gas.

7. The electronic cigarette atomization core of claim 3, wherein at least one through hole is provided in the second liquid guide body.

8. The electronic cigarette atomization core of claim 7, wherein at least one minipore which penetrates through the ultrasonic atomization piece is provided in the ultrasonic atomization piece.

9. The electronic cigarette atomization core of claim 7, wherein a vent groove is provided in the surface in which the ultrasonic atomization piece is in contact with the second liquid guide body.

10. The electronic cigarette atomization core of claim 7, wherein a depression part is provided at the middle of the second liquid guide body, and the through hole is provided in the depression part.

11. An electronic cigarette atomizer, wherein the electronic cigarette atomizer comprises an electronic cigarette atomization core, the electronic cigarette atomization core comprising:
an ultrasonic atomization piece comprising a piezoelectric ceramic main body; wherein:
one surface of the piezoelectric ceramic main body is in contact with a positive electrode conducting layer;
another surface of the piezoelectric ceramic main body is in contact with a negative electrode conducting layer,
the negative electrode conducting layer extends to the surface of the piezoelectric ceramic main body on which the positive electrode conducting layer is located along a side edge of the piezoelectric ceramic main body,
a plurality of convex point areas which cover an edge of the positive electrode conducting layer are provided on an edge of the negative electrode conducting layer;
a first sleeve, a second sleeve, a first liquid guide body, and a second liquid guide body; wherein:
one end of the first sleeve is provided in the second sleeve;
the first liquid guide body is fixed between the first sleeve and the second sleeve, and one end of the first liquid guide body is in contact with the second liquid guide body;
a liquid inlet hole is provided in the second sleeve, and the first liquid guide body is communicated with the liquid inlet hole; and
the second liquid guide body is in contact with the ultrasonic atomization piece;
a liquid storage cavity and an airflow passage;
wherein the liquid storage cavity is communicated with the liquid inlet hole; and one surface, away from the ultrasonic atomization piece, of the second liquid guide body is communicated with the airflow passage.

12. The electronic cigarette atomizer of claim 11, wherein:
the airflow passage comprises an air outlet pipe provided in the first sleeve;
an air inlet passage is provided between an inner wall of the first sleeve and an outer wall of the air outlet pipe;
a bottom end of the air outlet pipe is communicated with an upper surface of the second liquid guide body;
a top end of the air outlet pipe is in fixed connection with a suction nozzle base, and the air outlet pipe is communicated with the inner cavity of a suction nozzle on the suction nozzle base;
an air inlet is provided in the suction nozzle base; and
the air inlet passage is communicated with the air inlet and the surface, away from the ultrasonic atomization piece, of the second liquid guide body.

13. The electronic cigarette atomizer of claim 12, wherein:
a bottom end of the second sleeve is provided in a top part of an outer ring;
a second fixing ring is provided in the outer ring;
an insulating ring is provided in the second fixing ring;
a negative electrode spring is provided at the outside of the insulating ring;
a positive electrode spring is provided in the insulating ring; and
the negative electrode spring is in contact with the negative electrode conducting layer of the ultrasonic atomization piece through a negative electrode ring, and the positive electrode spring is in contact with the positive electrode conducting layer of the ultrasonic atomization piece through a positive electrode ring.

14. The electronic cigarette atomizer of claim 11, wherein:
the airflow passage comprises an air outlet pipe whose bottom end is provided in the top cover;
an air inlet passage is provided between the air outlet pipe and the top cover;
the bottom end of the air outlet pipe is communicated with the upper surface of the second liquid guide body;
the top end of the air outlet pipe is in fixed connection with a suction nozzle base, and the air outlet pipe is communicated with the inner cavity of a suction nozzle on the suction nozzle base;

an air inlet is formed in the suction nozzle base; and
the air inlet passage is communicated with the air inlet and the second liquid guide body.

15. The electronic cigarette atomizer of claim 14, wherein:
a base is provided in the first sleeve;
a bottom plug is provided on the base, and a top end of the bottom plug stretches into the insulating ring;
a negative electrode spring is provided at outside of the insulating ring;
a positive electrode spring is provided in the insulating ring; and
the negative electrode spring is in contact with the negative electrode conducting layer of the ultrasonic atomization piece through a negative electrode ring, and the positive electrode spring is in contact with the positive electrode conducting layer of the ultrasonic atomization piece through a positive electrode ring.

16. An electronic cigarette atomizer, wherein the electronic cigarette atomizer comprises the electronic cigarette atomization core of claim 6, a liquid storage cavity and an airflow passage; the liquid storage cavity is communicated with the liquid inlet hole; and one surface, away from the ultrasonic atomization piece, of the second liquid guide body is communicated with the airflow passage.

* * * * *